(12) United States Patent
Casse et al.

(10) Patent No.: US 8,216,802 B2
(45) Date of Patent: Jul. 10, 2012

(54) DETECTION MEDIUM FOR GRAM NEGATIVE BACTERIA

(75) Inventors: Marine Casse, Saint Pierre de Chartreuse (FR); Sylvain Orenga, Neuville sur Ain (FR); Celine Roger-Dalbert, Chazey sur Ain (FR)

(73) Assignee: Biomerieux, Marcy l'Etoile (FR)

( * ) Notice: Subject to any disclaimer, the term of this patent is extended or adjusted under 35 U.S.C. 154(b) by 359 days.

(21) Appl. No.: 12/448,851

(22) PCT Filed: Feb. 7, 2008

(86) PCT No.: PCT/FR2008/050183
§ 371 (c)(1),
(2), (4) Date: Jul. 10, 2009

(87) PCT Pub. No.: WO2008/104679
PCT Pub. Date: Sep. 4, 2008

(65) Prior Publication Data
US 2010/0062466 A1  Mar. 11, 2010

(30) Foreign Application Priority Data
Feb. 8, 2007 (FR) ..................... 07 53149

(51) Int. Cl.
*C12Q 1/04* (2006.01)
(52) U.S. Cl. ........................................ 435/34
(58) Field of Classification Search .............. 435/34, 435/38, 252.8
See application file for complete search history.

(56) References Cited

U.S. PATENT DOCUMENTS

| 5,210,022 A * | 5/1993 | Roth et al. ............ 435/34 |
| 5,888,760 A * | 3/1999 | Godsey et al. ......... 435/34 |
| 6,146,840 A * | 11/2000 | Chang et al. ......... 435/14 |
| 2010/0062467 A1 * | 3/2010 | Monget et al. ......... 435/18 |

FOREIGN PATENT DOCUMENTS

| EP | 0 704 538 A1 | 4/1996 |
| EP | 1 300 471 A1 | 4/2003 |
| EP | 1 323 832 A1 | 7/2003 |

OTHER PUBLICATIONS

Kantham L. et al. Beta Glucosidase of *Penicillium funiculosum*. Biotechnolgoy and Bioengineering 27(6)786-791, 1985.*
Kantham et al.; "β-Glucosidase of *Penicillium funiculosum*. II. Properties and Mycelial Binding;" *Biotechnology and Bioengineering*; 1985; pp. 786-791; vol. 27; No. 6.
Martin et al.; "Interet Des Milieux Contenant Des Substrats Chromogenes Pour L'identification Et La Numeration Des Bacteries Urinaires;" *Pathologie Et Biologie*; 1995; pp. 749-753; vol. 43; No. 9.

* cited by examiner

*Primary Examiner* — Ralph Gitomer
(74) *Attorney, Agent, or Firm* — Oliff & Berridge, PLC

(57) ABSTRACT

A detection medium including a substrate for a metabolic activity specific for a group of Gram-negative bacteria, a beta-glucosidase or cellobiosidase substrate, and a beta-glucosidase or cellobiosidase inducer. The inducer is a carbohydrate constituted of a carbohydrate linked in the β-position to glucose, or a carbohydrate with a βglucoside subunit, preferably selected from cellobiose, cellulose, starch, cellotriose, and trehalose.

13 Claims, No Drawings

DETECTION MEDIUM FOR GRAM NEGATIVE BACTERIA

This Application is a National Stage application filed under Rule 371 based upon PCT/FR2008/050183 filed Feb. 7, 2008.

The field of the invention is that of biochemical microbiological analysis, and in particular of the detection and identification of bacteria.

Pathogenic bacteria, and in particular Gram-negative bacilli, such as enterobacteria, Vibrionaceae or *Pseudomonas*, are responsible each year for many disesases, epidemics, etc.

*Pseudomonas* are ubiquitous bacteria that are encountered in soils, on plants and, especially, in freshwater and marine water. Many strains can develop at low temperature and, as a result, contaminate food stored in a refrigerator, and are responsible for gastrointestinal infections. They are also responsible for nosocomial infections.

The enterobacterial species most commonly isolated in clinical bacteriology belong to the genera *Citrobacter, Enterobacter, Escherichia, Hafnia, Klebsiella, Morganella, Proteus, Providencia, Salmonella, Serratia, Shigella* and *Yersinia*.

The *E. coli* species is the aerobic species most predominantly represented in the digestive tract. However, the presence thereof in water is an indication of fecal contamination, and certain strains are pathogenic and responsible for peritoneal, biliary, appendicular or genital suppurations.

Bacteria of the *Salmonella* genus are intestinal parasites of vertebrate animals and of birds and are transmitted to humans via contaminated food. They are then responsible for gastroenteritis diseases and typhoid and paratyphoid fevers.

Finally, *Citrobacter*, such as *Citrobacter freundii*, are commensal bacteria of the human and animal digestive tract that can be isolated from urine, from respiratory secretions or even from the blood, and that are responsible for infections in immunodepressed individuals.

Early and specific detection of these Gram-negative bacteria makes it possible to propose a suitable solution, in terms of treatment, of decontamination, etc.

Many media currently exist for detecting Gram-negative bacteria. This detection can be based especially on the use of particular substrates, specific for a metabolic activity, such as an enzymatic activity, of the bacterium that it is desired to detect: through the choice of substrates, depending on whether or not there is a reaction, it is possible to characterize the nature of a microorganism.

Mention may in particular be made of the UriSelect 4 medium (Bio-Rad), which uses a β-galactosidase substrate combined with a β-glucosidase substrate and with the detection of tryptophanase for detecting strains of the *E. coli* species and separating β-galactosidase positive/β-glucosidase negative *Citrobacter* strains.

Mention may also be made of the UTI medium (oxoid), which uses a β-galactosidase substrate combined with a β-glucosidase substrate and with the detection of tryptophanase for detecting strains of the *E. coli* species and separating β-galactosidase positive/β-glucosidase negative *Citrobacter* strains.

The CPS ID 3 medium (bioMérieux) uses a β-glucuronidase substrate combined with a β-glucosidase substrate and, optionally, with the detection of tryptophanase for detecting strains of the *Escherichia coli* species.

The BBL CHROMagar Orientation medium (Becton-Dickinson) uses a β-galactosidase substrate combined with a β-glucosidase substrate and with the detection of tryptophanase for detecting strains of the *E. coli* species and separating β-galactosidase positive/β-glucosidase negative *Citrobacter* strains.

Finally, the Urine Specific Agar medium (AES Laboratoire) uses a β-glucuronidase substrate combined with the detection of tryptophanase for detecting strains of the *E. coli* species and differentiating them from *Citrobacter* strains.

However, the chromogenic media using a β-glucuronidase substrate for detecting *E. coli* exhibit excellent specificity but imperfect sensitivity due to the existence of a small proportion of *E. coli* strains (5-10%) that do not express this activity. In addition, some *Citrobacter* strains can also produce β-glucuronidase positive colonies, having the same color as those of *E. coli*.

For the chromogenic media using a β-galactosidase substrate for detecting *E. coli*, it is necessary to confirm the identification by carrying out an additional test for differentiating *E. coli* from the other enterobacteria expressing β-galactosidase activity, and not expressing or weakly expressing β-glucosidase activity, in particular certain *Citrobacter* strains.

With regard to the detection of salmonellae, mention may be made of the SM ID medium, which uses glucuronate and a β-galactosidase substrate. However, a biochemical and/or serological confirmation is necessary for detecting strains of the *Salmonella* genus and differentiating them from the strains of other enterobacteria, in particular those of the *Citrobacter* genus.

Finally, with regard to *Pseudomonas*, mention may be made of the Cetrimide medium which uses Cetrimide and the detection of pyocyanin for detecting strains of the *Pseudomonas aeruginosa* species and differentiating them from the other Gram-negative bacteria. An improvement in the specificity of this medium would, however, be an advantage.

The invention proposes to solve the prior art problems by providing a new medium that is particularly suitable for identifying Gram-negative bacteria rapidly and inexpensively and in a manner that is easy to implement.

Surprisingly, the inventors have shown that a medium comprising a particular combination of metabolic activity substrates and of inducers enables rapid and easy detection of Gram-negative bacteria. More specifically, the inventors have in particular shown that the induction of β-glucosidase by a carbohydrate, in particular cellobiose, makes it possible to reduce the number of *Citrobacter* strains producing colonies of the same color as *E. coli*, thus enabling excellent separation of these two species.

Before proceeding with the disclosure of the invention, the following definitions are given in order to facilitate understanding of the invention.

The term detection medium is intended to mean a medium comprising all the elements necessary for the survival and/or the growth of microorganisms. This detection medium can either serve as detection medium only, or as culture and detection medium. In the first case, the culturing of the microorganisms is carried out before inoculation, and in the second case, the detection medium also constitutes the culture medium. The culture medium according to the invention may contain other possible additives, for instance: peptones or extracts of tissues, one or more growth factors, carbohydrates, one or more selective agents, buffers, one or more gelling agents, etc. This culture medium may be in liquid form or in the form of a ready-to-use gel, i.e. ready for seeding in a tube or flask or on a Petri dish.

For the purpose of the present invention, the detection can be carried out in liquid medium, on a strip, or on another solid support.

The term Gram-negative bacteria is intended to mean a group of bacteria which, during coloration by the Gram-stain method, do not retain crystal violet and appear pink. Such a group of Gram-negative bacteria may in particular comprise, or be constituted in particular of, enterobacteria, salmonellae (*Salmonella*), *Pseudomonas aeruginosa*.

As Gram-negative bacteria, mention may in particular be made of the family of enterobacteria (Enterobacteriaceae), the family Vibrionaceae, such as the species *Vibrio cholerae*, or else *Pseudomonas*, in particular *Pseudomonas aeruginosa*.

As enterobacteria, mention may in particular be made of the following genera: *Alishewanella; Alterococcus; Aquimonas; Aranicola; Arsenophonus; Azotivirga; Blochmannia (candidatus); Brenneria; Buchnera; Budvicia; Buttiauxella; Calymmatobacterium; Cedecea; Citrobacter; Dickeya; Edwardsiella; Enterobacter; Erwinia*, for example *Erwinia amylovora; Escherichia*, for example *Escherichia coli; Ewingella; Grimontella; Hafnia; Klebsiella*, for example *Klebsiella pneumoniae; Kluyvera; Leclercia; Leminorella; Levinea; Moellerella; Morganella; Obesumbacterium; Pantoea; Pectobacterium; Phlomobacter (candidatus); Photorhabdus; Plesiomonas*, for example *Plesiomonas shigelloides; Pragia; Proteus*, for example *Proteus vulgaris; Providencia; Rahnella; Raoultella; Saccharobacter; Salmonella; Samsonia; Serratia*, for example *Serratia marcescens; Shigella; Sodalis; Tatumella; Thorsellia, Trabulsiella; Wigglesworthia; Xenorhabdus; Yersinia*, for example *Yersinia pestis; Yokenella*.

The term group comprising *Citrobacter* is intended to mean a group comprising bacteria belonging to the *Citrobacter* genus. This group may also comprise other species. Thus, a preferred group comprising Citrobacter is a group comprising, or constituted of, *Citrobacter, Enterobacter, Klebsiella* and *Serratia* bacteria (also known as KESC group). The term substrate is intended to mean any molecule capable of directly or indirectly generating a detectable signal due to an enzymatic or metabolic activity of the microorganism.

The substrate may in particular be a metabolic substrate, such as a carbon or nitrogen source, coupled to an indicator that produces a coloration in the presence of one of the products of the metabolism.

The substrate may also be an enzymatic substrate, i.e. a substrate that can be hydrolyzed by an enzyme so as to give a product that enables direct or indirect detection of a microorganism. This substrate may in particular comprise a first part which is specific for the enzymatic activity to be revealed and a second part which acts as a label, hereinafter known as label part. This label part may be chromogenic, fluorogenic, luminescent, etc. As chromogenic substrate suitable for solid supports (filter, agar, electrophoresis gel), mention may in particular be made of substrates based on indoxyl and its derivatives, and substrates based on hydroxyquinoline or on esculetin and their derivatives, which enable the detection of osidase and esterase activities. Mention may also be made of substrates based on nitrophenol and nitroaniline and derivatives, for detecting osidase and esterase activities in the case of nitrophenol-based substrates, and peptidase activities in the case of nitroaniline-based substrates. Finally, mention may be made of substrates based on naphthol and naphthylamine and their derivatives, which make it possible to detect osidase and esterase activities by means of naphthol, and peptidase activities by means of naphthylamine. This substrate may in particular, but in a nonlimiting manner, enable the detection of an enzymatic activity such as the activity of an osidase, peptidase, esterase, etc. The enzymatic substrate may also be a natural substrate, the product of hydrolysis of which is detected directly or indirectly. As a natural substrate, mention may in particular be made of tryptophan for detecting a tryptophanase or deaminase activity, a cyclic amino acid (tryptophan, phenylalanine, histidine, tyrosine) for detecting a deaminase activity, phosphatidylinositol for detecting a phospholipase activity, etc.

According to the present invention, the substrate is preferably selected from substrates based on indoxyl (3-indoxyl, 5-bromo-3-indoxyl, 4-chloro-3-indoxyl, 5-iodo-3-indoxyl, 5-bromo-4-chloro-3-indoxyl, 5-bromo-6-chloro-3-indoxyl, 6-bromo-3-indoxyl, 6-chloro-3-indoxyl, 6-fluoro-3-indoxyl, 5-bromo-4-chloro-N-methyl-3-indoxyl, N-methyl-3-indoxyl, etc); on umbelliferone (4-methylumbelliferone, cyclohexenoesculetin, etc); on alizarine; on p-naphtholbenzein; on nitrophenol (ortho-nitrophenol, para-nitrophenol, etc.); on naphthol (alpha-naphthol, 2-naphthol, naphthol-ASBI, etc); on aminophenol (para-aminophenol, dichloroaminophenol, etc.); on hydroxyquinoline; on catechol (catechol, dihydroxyflavone, hydroxyflavone, etc.); on resorufin; on Chlorophenol Red; on fluorescein; on aminocoumarin (7-amino-4-methylcoumarin, etc.); on naphthylamide; on acridine (aminophenylacridine); or on aminophenoxazine (aminobenzophenoxazinone, aminopentylresorufin, etc.).

The term metabolic activity is intended to mean a collection of chemical reactions that take place in a bacterium. These chemical reactions can be linked to one or more enzymatic activities, to the degradation, synthesis, or modification of a molecule.

The expression metabolic activity specific for a group of Gram-negative bacteria is intended to mean a metabolic activity preferentially produced by this group of Gram-negative bacteria.

For a group comprising or constituted of *E. coli*, mention may in particular be made of beta-glucuronidase, beta-galactosidase, alpha-galactosidase, acidification of lactose, tryptophanase, beta-ribosidase, phosphatase, L-alanine aminopeptidase and L-leucine aminopeptidase. Preferably, the metabolic activity is beta-glucuronidase or beta-galactosidase.

The substrates used for detecting beta-glucuronidase activity may in particular be 4-methylumbelliferyl-beta-glucuronide, 5-bromo-4-chloro-3-indolyl-beta-glucuronide, 5-bromo-6-chloro-3-indolyl-beta-glucuronide, 6-chloro-3- indolyl-beta-glucuronide, alizarine-beta-glucuronide, or cyclohexenoesculetin-beta-glucuronide, or salts thereof, at concentrations of preferably between 10 and 1000 mg/l.

The substrates used for detecting beta-galactosidase activity may in particular be 4-methylumbelliferyl-beta-galactoside, 5-bromo-4-chloro-3-indolyl-beta-galactoside, 5-bromo-6-chloro-3-indolyl-beta-galactoside, 6-chloro-3-indolyl-beta-galactoside, alizarine-beta-galactoside or cyclohexenoesculetin-beta-galactoside or salts thereof, at concentrations of preferably between 10 and 1000 mg/l.

For a group comprising or constituted of *Salmonella*, mention may also be made of alpha-galactosidase, esterase, acidification of glucuronate, sorbitol, propanediol, melibiose and mannitol. As alpha-galactosidase substrate, mention may be made of 4-methylumbelliferyl-alpha-galactoside, 5-bromo-4-chloro-3-indolyl-alpha-galactoside, 5-bromo-6-chloro-3-indolyl-alpha-galactoside, 6-chloro-3-indolyl-alpha-galactoside, alizarine-alpha-galactoside or nitrophenyl-alpha-galactoside, at concentrations of between 10 and 1000 mg/l.

Among the esterase substrates, mention may be made of 4-methylumbelliferyl octanoate, 5-bromo-4-chloro-3-indoxyl octanoate, 5-bromo-4-chloro-3-indoxyl nonanoate, 5-bromo-6-chloro-3-indoxyl octanoate, 5-bromo-6-chloro-3-indoxyl hexanoate, 6-chloro-3-indoxyl octanoate or alizarine octanoate, at concentrations of between 20 and 1000 mg/l.

For a group comprising or constituted of *Pseudomonas aeruginosa*, mention may also be made of esterase, aminopeptidase or oxidase.

Among the esterase substrates, mention may be made of 4-methylumbelliferyl octanoate, 5-bromo-4-chloro-3-indoxyl octanoate, 5-bromo-4-chloro-3-indoxyl nonaoate, 5-bromo-6-chloro-3-indoxyl octanoate, 5-bromo-6-chloro-3-indoxyl hexanoate, 6-chloro-3-indoxyl octanoate or alizarine octanoate, at concentrations of between 20 and 1000 mg/l.

Among the aminopeptidase substrates, mention may in particular be made of beta-alanylamidophenol, beta-alanyl-dichloroamidophenol, beta-alanyl-para-nitroanilide, beta-alanyl-beta-naphthylamide, 7-N-(beta-alanyl)aminophenoxazine-1-pentyl-3-one or 7-N-(L-pyroglutamypaminophenoxazine-1-pentyl-3-one, at concentrations of between 10 and 1000 mg/l.

The term inducer is intended to mean a compound which induces an increase in the expression of the targeted metabolic activity; all experimental conditions being otherwise equal, the metabolic activity is stronger when the inducer is at an appropriate concentration than when it is absent or at an unsuitable concentration.

Mention may in particular be made of:
  for beta-glucosidase or cellobiosidase, a carbohydrate constituted of a carbohydrate linked in the β-position to glucose, or a carbohydrate with a β-glucoside subunit, in particular cellobiose, cellulose, starch, cellotriose or trehalose.
  Mention may also be made of methyl-β-glucoside, isopropyl-β-thioglucoside, indoxyl-β-glucoside or methyl-β-thioglucoside;
  for beta-glucuronidase, glucuronate, methyl-beta-glucuronide or other beta-glucuronides;
  for beta-galactosidase, lactose, isopropyl-beta-thiogalactoside or other beta-galactosides.

Without being limiting, a concentration of between 100 ng/l and 10 g/l, preferably between 10 mg/l and 3 g/l, it is particularly suitable for the present invention.

The term biological sample is intended to mean a clinical sample, derived from a sample of biological fluid, or a food sample, derived from any type of food, or an environmental sample such as a surface sample, water sample, air sample, etc. This sample may thus be liquid or solid and mention may be made, in a nonlimiting manner, of a clinical sample from blood, plasma, urine or feces, samples taken from the nose, from the throat, from the skin, from wounds or from cerebrospinal fluid, a food sample from water, or from drinks such as milk or a fruit juice; from yoghurt, meat, eggs, vegetables, mayonnaise or cheese; from fish, etc., or a food sample derived from an animal feed, such as in particular a sample derived from animal meals.

The invention relates to a detection medium comprising:
  a substrate for a metabolic activity specific for a group of Gram-negative bacteria;
  a beta-glucosidase or cellobiosidase substrate;
  a beta-glucosidase or cellobiosidase inducer, said inducer being a carbohydrate constituted of a carbohydrate linked in the β-position to glucose, or a carbohydrate with a β-glucoside subunit.

The substrates used for detecting beta-glucosidase activity may in particular be 4-methylumbelliferyl-beta-glucoside, 5-bromo-4-chloro-3-indolyl-beta-glucoside, 5-bromo-6-chloro-3-indolyl-beta-glucoside, 6-chloro-3-indolyl-beta-glucoside, alizarine-beta-glucoside, cyclohexenoesculetin-beta-glucoside, nitrophenyl-beta-glucoside or dichloroaminophenylglucoside, or salts thereof, at concentrations of preferably between 10 and 1000 mg/l.

By way of cellobiosidase substrates, mention may in particular be made of 4-methylumbelliferyl-beta-cellobioside, 5-bromo-4-chloro-3-indolyl-beta-cellobioside, 5-bromo-6-chloro-3-indolyl-beta-cellobioside, 6-chloro-3-indolyl-beta-cellobioside or nitrophenyl-beta-cellobioside.

According to one preferred embodiment of the invention, said beta-glucosidase or cellobiosidase inducer is at a concentration of between 100 ng/l and 10 g/l, preferably between 10 mg/l and 3 g/l.

Preferably, said inducer is selected from cellobiose, cellulose, starch, cellotriose and trehalose.

According to one preferred embodiment of the invention, said beta-glucosidase or cellobiosidase inducer is cellobiose. Preferably, the cellobiose is at a concentration of between 100 ng/l and 10 g/l, even more preferably between 10 mg/l and 3 g/l.

According to one preferred embodiment of the invention, said group of Gram-negative bacteria comprises enterobacteria. According to one even more preferred embodiment of the invention, said group of Gram-negative bacteria is constituted of enterobacteria.

According to one preferred embodiment, the enterobacteria are *E. coli*. Thus, said group of enterobacteria may comprise or be constituted of *E. coli*. In this embodiment, said substrate for the metabolic activity is specific for *E. coli* and is preferably selected from a substrate for beta-glucuronidase, beta-galctosidase or alpha-galactosidase, for acidification of lactose, or for tryptophanase, beta-ribosidase, phosphatase, L-alanine aminopeptidase or L-leucine aminopeptidase. Preferably, said substrate is a substrate for beta-glucuronidase or beta-galactosidase.

According to another preferred embodiment, the enterobacteria are *Salmonella*. Thus, said group of enterobacteria may comprise or be constituted of *Salmonella*. In this embodiment, said substrate for the metabolic activity is specific for *Salmonella* and is preferably selected from a substrate for alpha-galactosidase, esterase or acidification of glucuronate, or sorbitol, propanediol, melibiose or mannitol.

According to another preferred embodiment of the invention, said group of Gram-negative bacteria comprises or is constituted of *Pseudomonas aeruginosa*. Preferably, said substrate for the metabolic activity is specific for *Pseudomonas aeruginosa* and is selected from a substrate for esterase, aminopeptidase or oxidase.

According to one preferred embodiment of the invention, the detection medium also comprises an inducer of said metabolic activity specific for the group of Gram-negative bacteria, said group of Gram-negative bacteria preferably comprising enterobacteria.

According to one particular embodiment of the invention, the inducer for beta-glucuronidase is preferably selected from glucuronate, methyl-beta-glucuronide or other beta-glucuronides.

According to another particular embodiment of the invention, the inducer for beta-galactosidase is preferably selected from lactose, isopropyl-beta-thiogalactoside or other beta-galactosides.

According to one preferred embodiment of the invention, the detection medium also comprises a second β-glucosidase or cellobiosidase inducer, such as methyl-β-glucoside, isopropyl-β-thioglucoside, indoxyl-β-glucoside or methyl-β-thioglucoside. Preferably, said inducer is methyl-beta-glucoside.

Preferably, said second inducer is at a concentration of between 100 ng/l and 10 g/l, preferably between 100 mg/l and 3 g/l, even more preferably between 50 and 200 mg/l.

The invention also relates to the use of a medium as defined above, for distinguishing between a group of bacteria comprising *Citrobacter* and another group of Gram-negative bacteria. According to one preferred embodiment of the invention, the medium is used for distinguishing a group comprising or constituted of *Citrobacter* from a group comprising or constituted of *E. coli*.

According to another embodiment of the invention, the medium is used for distinguishing a group comprising or constituted of *Citrobacter* from a group comprising or constituted of *Salmonella*.

According to another embodiment of the invention, the medium is used for distinguishing a group comprising or constituted of *Citrobacter* from a group comprising or constituted of *P. aeruginosa*.

The invention also relates to a culture medium comprising:
a beta-glucosidase substrate;
a beta-glucosidase or cellobiosidase inducer, said inducer being a carbohydrate constituted of a carbohydrate linked in the β-position to glucose, or a carbohydrate with a β-glucoside subunit, preferably selected from cellobiose, cellulose, starch, cellotriose and trehalose, at a concentration of between 10 mg/l and 10 g/l.

This medium is particularly suitable for distinguishing between a group comprising or constituted of *Citrobacter* bacteria and another group of Gram-negative bacteria. In this respect, the invention also relates to the use of a medium as defined above, for distinguishing between a group of bacteria comprising *Citrobacter* and another group of Gram-negative bacteria.

Preferably, the invention relates to the use of a medium as defined above, for distinguishing:
a group comprising or constituted of *Citrobacter* from a group comprising or constituted of *E. coli*;
a group comprising or constituted of *Citrobacter* from a group comprising or constituted of *Salmonella*;
a group comprising or constituted of *Citrobacter* from a group comprising or constituted of *P. aeruginosa*.

The invention also relates to the use of a medium comprising:
a beta-glucosidase substrate;
a beta-glucosidase or cellobiosidase inducer, said inducer being a carbohydrate constituted of a carbohydrate linked in the β-position to glucose, or a carbohydrate with a β-glucoside subunit, preferably selected from cellobiose, cellulose, starch and cellotriose,
for distinguishing between a group of bacteria comprising *Citrobacter* and another group of Gram-negative bacteria, preferably for distinguishing:
a group comprising or constituted of *Citrobacter* from a group comprising or constituted of *E. coli*;
a group comprising or constituted of *Citrobacter* from a group comprising or constituted of *Salmonella*;
a group comprising or constituted of *Citrobacter* from a group comprising or constituted of *P. aeruginosa*.

The invention also relates to a method for distinguishing between a group of bacteria comprising *Citrobacter* and a group of Gram-negative bacteria, in a biological sample, according to which:
the biological sample is inoculated on a detection medium as defined above, so as to obtain bacterial colonies, or on a medium comprising a beta-glucosidase substrate and a beta-glucosidase or cellobiosidase inducer, said inducer being a carbohydrate constituted of a carbohydrate linked in the β-position to glucose, or a carbohydrate with a β-glucoside subunit, preferably selected from cellobiose, cellulose, starch and cellotriose, so as to obtain bacterial colonies;
the colonies that react with said beta-glucosidase substrate are identified as belonging to a group comprising or constituted of *Citrobacter* and the colonies that react with said substrate specific for Gram-negative bacteria are identified as being Gram-negative bacteria.

Preferably, the method is used for distinguishing:
a group comprising or constituted of *Citrobacter* from a group comprising or constituted of *E. coli*;
a group comprising or constituted of *Citrobacter* from a group comprising or constituted of *Salmonella*;
a group comprising or constituted of *Citrobacter* from a group comprising or constituted of *P. aeruginosa*.

The inoculation of the microorganisms can be carried out by any of the inoculation techniques known to those skilled in the art. An incubation step may be carried out at a temperature for which the enzymatic activity that it is desired to detect is optimal, it being possible for those skilled in the art to easily select said temperature depending on the enzymatic activity to be detected.

The identification may be carried out by means of a visual examination, or by colorimetry or fluorimetry.

EXAMPLES

The examples below are given by way of explanation and are in no way limiting in nature. They will make it possible to understand the invention more clearly.

Example 1

Contribution of Cellobiose for Distinguishing between *Escherichia coli* and *Citrobacter*

Various concentrations of cellobiose (0-100-350-1000 mg/l) are added to the CPS ID 3 medium (bioMérieux). These media contain 6-chloro-3-indolyl-beta-glucuronide at 250 mg/l and 5-bromo-4-chloro-3-indolyl-beta-glucoside at 50 mg/l. These media are distributed in a proportion of 20 ml per Petri dish. Microorganisms derived from the applicant's collection were inoculated on these media by semi-quantitative isolation of 10 µl of a suspension at 0.5 McFarland, diluted to 1/20. The dishes were incubated at 37° C. for 48 hours. The colonies formed were examined visually after 24 and 48 hours of incubation. The coloration of these colonies was noted. The results are given in table 1 below:

TABLE 1

Impact of cellobiose concentration in CPS ID 3 medium on colony coloration

| | | | Cellobiose concentration | | | |
|---|---|---|---|---|---|---|
| Strains | | | 0 | 100 | 350 | 1000 |
| Escherichia coli 407 | 24 h | Pink | Pink | Pink | Pink |
| | 48 h | Red | Red | Red | Red |
| Escherichia coli 003 | 24 h | Pink | Pink | Pink | Pink |
| | 48 h | Red | Red | Red | Red |
| Klebsiella pneumoniae 111 | 24 h | Turquoise | Turquoise | Turquoise | Turquoise |
| | 48 h | Turquoise | Turquoise | Turquoise | Turquoise |

TABLE 1-continued

Impact of cellobiose concentration in CPS ID 3 medium on colony coloration

| | | | Cellobiose concentration | | | |
|---|---|---|---|---|---|---|
| Strains | | | 0 | 100 | 350 | 1000 |
| Serratia marcescens 112 | 24 h | Turquoise | Turquoise | Turquoise | Turquoise |
| | 48 h | Turquoise | Turquoise | Turquoise | Turquoise |
| Citrobacter freundii 022 | 24 h | Pink | Violet | Violet | Violet |
| | 48 h | Mauve | Violet | Violet | Violet |
| Citrobacter freundii 031 | 24 h | Colorless | Green | Green | Colorless |
| | 48 h | Green | Green | Green | Green |
| Citrobacter freundii 104 | 24 h | Colorless | Green | Green | Green |
| | 48 h | Green | Green | Green | Green |
| Enterococcus faecalis 117 | 24 h | Turquoise | Turquoise | Turquoise | Turquoise |
| | 48 h | Turquoise | Turquoise | Turquoise | Turquoise |

In table 1 above, it appears that, in the presence of cellobiose, the *Citrobacter* strains express beta-glucosidase activity, which is reflected by a green to violet coloration of the colonies, depending on whether or not the strain expresses beta-glucuronidase activity in parallel. Thus, in the absence of cellobiose, the *C. freundii* 022 strain (pink colonies at 24H) can be confused with the *Escherichia coli* strains, which is no longer the case in the presence of cellobiose.

Example 2

Impact of Cellobiose Concentration on the Distinction Between *Citrobacter* and Other Enterobacteria Various concentrations of cellobiose (0-0.1-1-5-10 g/l) are added to Trypticase Soy medium (bioMérieux) supplemented with 5-bromo-6-chloro-3-indolyl-beta-galactoside at 50 mg/l and with 5-bromo-4-chloro-3-indolyl-beta-glucoside at 50 mg/l. These media are distributed in a proportion of 20 ml per Petri dish. Microorganisms derived from the applicant's collection were inoculated on these media by semi-quantitative isolation of 10 µl of a suspension at 0.5 McFarland, diluted to 1/20. The dishes were incubated at 37° C. for 48 hours. The colonies formed were examined visually after 24 and 48 hours of incubation. The coloration of these colonies was noted. The results are given in table 2 below:

TABLE 2

Impact of cellobiose concentration in Trypticase soy medium supplemented with 5-bromo-6-chloro-3-indolyl-beta-galactoside and with 5-bromo-4-chloro-3-indolyl-beta-glucoside, on colony coloration

| | | | Cellobiose concentration | | | |
|---|---|---|---|---|---|---|
| Strains | | | 0 | 0.1 | 1 | 5 | 10 |
| Escherichia coli 018 | 24 h | Mauve | Mauve | Mauve | Mauve | Mauve |
| | 48 h | Mauve | Mauve | Mauve | Mauve | Mauve |
| Escherichia coli 003 | 24 h | Mauve | Mauve | Mauve | Mauve | Mauve |
| | 48 h | Mauve | Mauve | Mauve | Mauve | Mauve |
| Klebsiella pneumoniae 111 | 24 h | Green | Green | Green | Turquoise | Turquoise |
| | 48 h | Blue | Blue | Blue | Blue | Blue |
| Serratia marcescens 112 | 24 h | Green | Green | Green | Green | Turquoise |
| | 48 h | Blue | Blue | Blue | Blue | Blue |
| Citrobacter freundii 022 | 24 h | Mauve | Violet | Violet | Pink | Mauve |
| | 48 h | Mauve | Blue | Blue | Blue | Mauve |

TABLE 2-continued

Impact of cellobiose concentration in Trypticase soy medium
supplemented with 5-bromo-6-chloro-3-indolyl-beta-galactoside and
with 5-bromo-4-chloro-3-indolyl-beta-glucoside, on colony coloration

| Strains | | Cellobiose concentration | | | | |
|---|---|---|---|---|---|---|
| | | 0 | 0.1 | 1 | 5 | 10 |
| Citrobacter freundii 031 | 24 h | Mauve | Violet | Mauve | Mauve | Mauve |
| | 48 h | Mauve | Green | Green | Green | Mauve |
| Citrobacter freundii 104 | 24 h | Mauve | Violet | Violet | Mauve | Mauve |
| | 48 h | Mauve | Green | Green | Green | Mauve |
| Enterococcus faecalis 117 | 24 h | Turquoise | Turquoise | Turquoise | Turquoise | Turquoise |
| | 48 h | Turquoise | Turquoise | Turquoise | Turquoise | Turquoise |

In table 2 above, it appears that, in the presence of cellobiose, the *Citrobacter* strains express beta-glucosidase activity, which is reflected by a green to violet coloration of the colonies, depending on whether or not the strain expresses beta-galactosidase activity in parallel. Thus, in the absence of cellobiose, the *C. freundii* strains (mauve colonies at 24H) can be confused with the *E. coli* strains, which is no longer the case in the presence of cellobiose. However, the differentiation is less marked for cellobiose concentrations above 5 g/l.

The invention claimed is:

1. A detection medium for detecting Gram-negative bacteria comprising:
    a substrate for a metabolic activity specific for a group of Gram-negative bacteria;
    a beta-glucosidase or cellobiosidase substrate; and
    a beta-glucosidase or cellobiosidase inducer, said inducer being a carbohydrate constituted of a carbohydrate linked in the β-position to glucose, or a carbohydrate with a βglucoside subunit.

2. The medium as claimed in claim 1, wherein said beta-glucosidase or cellobiosidase inducer is at a concentration of between 100 ng/l and 10 g/l.

3. The medium as claimed in claim 1, wherein said beta-glucosidase or cellobiosidase inducer is cellobiose.

4. The medium as claimed in claim 1, wherein said group of Gram-negative bacteria comprises enterobacteria.

5. The medium as claimed in claim 4, wherein the enterobacteria are *E. coli*.

6. The medium as claimed in claim 5, wherein said substrate for the metabolic activity is specific for *E. coli* and is selected from a substrate for beta-glucuronidase, beta-galactosidase or alpha-galactosidase, for acidification of lactose, or for tryptophanase, beta-ribosidase, phosphatase, L-alanine aminopeptidase or L-leucine aminopeptidase.

7. The medium as claimed in claim 4, wherein the enterobacteria are *Salmonella*.

8. The medium as claimed in claim 7, wherein said substrate for the metabolic activity is specific for *Salmonella* and is selected from a substrate for alpha-galactosidase, esterase or acidification of glucuronate, or sorbitol, propanediol, melibiose or mannitol.

9. The medium as claimed in claim 1, wherein said group of Gram-negative bacteria comprises *Pseudomonas aeruginosa*.

10. The medium as claimed in claim 9, wherein said substrate for the metabolic activity is specific for *Pseudomonas aeruginosa* and is selected from a substrate for esterase, aminopeptidase or oxidase.

11. The medium as claimed in claim 1, wherein the detection medium further comprises an inducer of said metabolic activity specific for Gram-negative bacteria.

12. The medium as claimed in claim 1, wherein the detection medium further comprises a second β-glucosidase or cellobiosidase inducer.

13. A method for distinguishing between a group of bacteria comprising *Citrobacter* and another group of Gram-negative bacteria, in a biological sample, comprising:
    inoculating the biological sample on a detection medium as defined in claim 1 to obtain bacterial colonies;
    identifying the colonies that react with said beta-glucosidase substrate and correlating the colonies that react with said beta-glucosidase substrate as belonging to a group comprising or constituted of *Citrobacter*; and
    identifying the colonies that react with said substrate specific for Gram-negative bacteria and correlating the colonies that react with said substrate specific for Gram-negative bacteria as being Gram-negative bacteria.

* * * * *